United States Patent
Chatziantoniou et al.

(10) Patent No.: US 9,926,562 B2
(45) Date of Patent: Mar. 27, 2018

(54) METHODS FOR PREVENTING AND TREATING CHRONIC KIDNEY DISEASE (CKD)

(71) Applicants: INSERM (INSTITUT NATIONAL DE LA SANTE ET DE LA RECHERCHE MEDICALE), Paris (FR); ASSISTANCE PUBLIQUE—HOPITAUX DE PARIS, Paris (FR); INDIANA UNIVERSITY RESEARCH AND TECHNOLOGY CORPORATION, Indianapolis, IN (US)

(72) Inventors: Christos Chatziantoniou, Paris (FR); Jean-Claude Dussaule, Paris (FR); Simon J. Conway, Indianapolis, IN (US)

(73) Assignees: INSERM (INSTITUT NATIONAL DE LA SANTE ET DE LA RECHERCHE MEDICALE), Paris (FR); ASSITANCE PUBLIQUE—HOPITAUX DE PARIS, Paris (FR); INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 15/353,788

(22) Filed: Nov. 17, 2016

(65) Prior Publication Data

US 2017/0067053 A1 Mar. 9, 2017

Related U.S. Application Data

(62) Division of application No. 14/415,269, filed as application No. PCT/EP2013/065152 on Jul. 18, 2013, now abandoned.

(60) Provisional application No. 61/679,211, filed on Aug. 3, 2012.

(30) Foreign Application Priority Data

Jul. 18, 2012 (EP) ..................... 12305869

(51) Int. Cl.
| | | |
|---|---|---|
| C12N 15/11 | (2006.01) |
| C12N 15/113 | (2010.01) |
| C07K 16/18 | (2006.01) |
| C12N 15/115 | (2010.01) |

(52) U.S. Cl.
CPC ............ *C12N 15/113* (2013.01); *C07K 16/18* (2013.01); *C12N 15/115* (2013.01); *C12N 15/1138* (2013.01); *C07K 2317/76* (2013.01); *C12N 2310/11* (2013.01); *C12N 2310/16* (2013.01); *C12N 2310/315* (2013.01)

(58) Field of Classification Search
CPC ................................................... C12N 15/113
See application file for complete search history.

(56) References Cited

U.S. PATENT DOCUMENTS

| | | | |
|---|---|---|---|
| 6,506,559 B1 * | 1/2003 | Fire .................... | A61K 31/7105 435/325 |
| 2009/0074788 A1 * | 3/2009 | Taniyama ............ | C07K 16/18 424/152.1 |
| 2011/0130335 A1 * | 6/2011 | Kudo ................... | A61K 48/005 514/16.4 |
| 2012/0058572 A1 * | 3/2012 | Taniyama ............ | C07K 16/18 436/501 |

FOREIGN PATENT DOCUMENTS

WO WO2005/019471 A2 * 3/2005

OTHER PUBLICATIONS

Sen et al. (American Journal of Pathology 2011, 179: 1756-1767).*
Mael-Anin et al. Nephology Dialysis Transplation May 2012 Vo. 27 No. Suppl. 2, pp. 44., Meeting Info: 49$^{th}$ Congress of the European Renal Association, Paris France May 24-27, 2012.*
http://www.mayoclinic.org/diseases-conditions/kidney-disease/basics/definition/con-20026778, retrieved on Jun. 29, 2016, pp. 1-9.*
The Centers for Disease Control CDC, https://nccd.cdc.gov/CKD/help.aspx?section=F, accessed Jun. 29, 2016, pp. 1-3.*

* cited by examiner

*Primary Examiner* — Brian A Whiteman
(74) *Attorney, Agent, or Firm* — Whitham, Curtis & Cook, P.C.

(57) ABSTRACT

The present invention relates to methods for preventing and treating chronic kidney disease (CKD).

15 Claims, 7 Drawing Sheets

A

B

METHODS FOR PREVENTING AND TREATING CHRONIC KIDNEY DISEASE (CKD)

FIELD OF THE INVENTION

Figure 1:
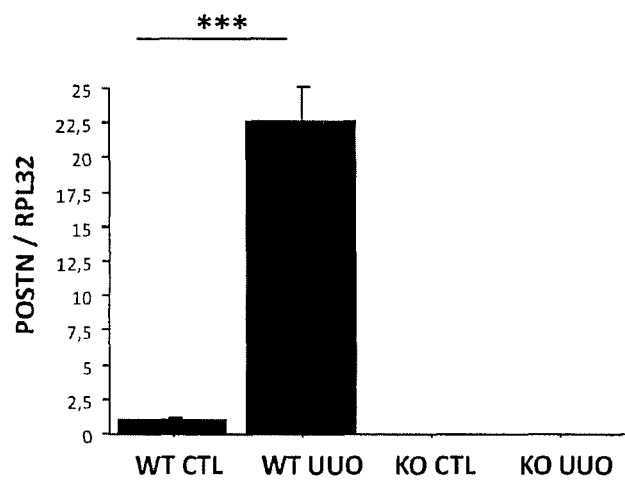
Figure 1:
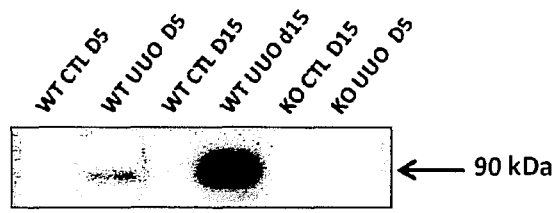

The present invention relates to methods for preventing and treating chronic kidney disease (CKD).

BACKGROUND OF THE INVENTION

Chronic Kidney Disease (CKD) can result from different causes, but the final pathway remains renal fibrosis characterized by chronic inflammation leading to abnormal accumulation of extracellular matrix (ECM). This fibrotic process leading to a decrease in the number of functioning nephrons is still not clear and constitutes the key of CKD progression. Thus, new insights into the pathophysiological mechanisms of renal fibrogenesis will guide us to a more efficient therapy. The amount of ECM is regulated by the balance between protein synthesis and degradation and it's particularly important during embryonic development and pathological states. While fibrogenesis mechanisms have been the subject of ongoing studies, attention has become focused on ECM proteins, due to their importance not only as components of fibrosis, but also as active regulators of tissue remodeling via cell-matrix signaling. In light of the foregoing, a need in the art exists for identifying a factor liable to be responsible for progression of renal fibrosis and therefore for the progression of CKD so as to envisage new tools for the treatment of such a disease.

Periostin (POSTN) also called Osteoblast-Specific Factor 2 (OSF-2) is a 90 kDa extracellular protein expressed during development and in very early postnatal tissue; its expression in healthy adult tissues is very low but increases considerably following injury.

Periostin expression has previously been shown to be significantly increased by both transforming growth factor beta-1 (TGFbeta1) and bone morphogenetic protein (BMP-2). Many studies in the heart showed that periostin is secreted by fibroblasts and regulates collagen deposition, thereby altering mechanical properties of connective tissues. When periostin was knocked out, animals showed reduced fibrosis after myocardial infarction. This matricellular protein has also the ability to associate to other ECM components as tenascin, fibronectin and to interact with integrins such as avb3 avbv, resulting in activation of Akt or PI3 kinase pathways. Recently, periostin was described in a wild range of pathologies (cancers, asthma . . . ) but little is known about periostin in the kidney, and its potential role in the progression of chronic kidney disease. To date, periostin was described in human autosomal dominant polycystic kidney and was shown to be de novo expressed in cyst epithelial cells (Wallace et al. 2008). Another study described gene expression profiles of several matricellular proteins on biopsies from patients with glomerulopathies and renal dysfunction; it showed that periostin was highly induced in tubuloibterstitial and fibrotic compartments and negatively correlated with renal function. Recently, periostin was identified in hypertensive nephropathy induced by L-NAME as an indicator of CKD progression and regression (Guerrot et al. 2012). It was indeed shown that periostin expression correlates with functional markers of kidney disease (plasma creatinine, proteinuria, renal blood flow) and that its localization was associated with perivascular fibrotic areas, hallmark of experimental hypertensive nephropathy. Interestingly, periostin was overexpressed in human kidney disease and was found in the injured fibrotic tubulointerstitial regions of chronic allograft nephropathy. Together, these results indicate that periostin is a good marker of progression and probably regression of renal fibrosis. These studies however, did not address the issue whether or not periostin participates in the development of renal fibrosis and CKD.

SUMMARY OF THE INVENTION

The present invention relates to an agent which binds to periostin selected from the group consisting of antibodies, aptamers, small organic molecules and polypeptides for use in the prevention or treatment of chronic kidney disease (CKD) in a subject in need thereof.

The present invention also relates to an inhibitor of periostin gene expression for use in the prevention or the treatment of a CKD in a subject in need thereof.

The present invention further relates to an agent which binds to periostin selected from the group consisting of antibodies, aptamers, small organic molecules and polypeptides or an inhibitor of periostin gene expression for preventing or reducing renal fibrosis.

DETAILED DESCRIPTION OF THE INVENTION

The inventors focused on the implication of periostin in the establishment of renal fibrosis. To this end, they investigated its role and mechanisms in experimental tubulointerstitial nephropathy; therefore they performed unilateral ureteral obstruction model (UUO) on wild-type (WT) and periostin knock-out (KO) mice, and showed that mice lacking periostin are protected against the development of renal fibrosis and renal disease.

Then, the inventors showed that administration of an inhibitor of periostin gene inhibitor (i.e. an antisense oligonucleotide) in a hypertensive nephropathy rat model (L-NAME-treated rats) is also useful for protecting them against the development of renal fibrosis and renal disease. Together, these data provide initial evidence that periostin can be a promising target against CKD progression.

Accordingly, a first object of the present invention relates to an agent which binds to periostin selected from the group consisting of antibodies, aptamers, small organic molecules, and polypeptides for use in the prevention or treatment of chronic kidney disease (CKD) in a subject in need thereof.

As used herein, the term "periostin" is intended to encompass all synonyms including, but not limited to, "osteoblast specific factor 2", "OSF-2" or "POSTN", and includes naturally occurring periostin as well as variants thereof.

The term "periostin protein" refers to the periostin protein of 834 amino acids provided in the GenPept database under accession number NP_006466.

As used herein, the term "prevention" refers to preventing the disease or condition from occurring in a subject which has not yet been diagnosed as having it.

As used herein, the term "treatment" refers to inhibiting the disease or condition, i.e. arresting its development; relieving the disease or condition, i.e. causing regression of the condition; or relieving the conditions caused by the disease, i.e. symptoms of the disease.

As used herein, the term "chronic kidney disease" (CKD) refers to a progressive loss in renal function over a period of months or years. CKD has its general meaning in the art and is used to classify numerous conditions that affect the kidney, destruction of the renal parenchyma and the loss of functional nephrons or glomeruli. It should be further noted that CKD can result from different causes, but the final pathway remains renal fibrosis. Examples of etiology of CKD include, but are not limited to, cardiovascular diseases, hypertension, diabetes, glomerulonephritis, polycystic kidney diseases, and kidney graft rejection.

As used herein, the terms "renal fibrosis" or "renal fibrogenesis" refer to a pathologic mechanism characterized by a chronic inflammation leading to abnormal accumulation of extracellular matrix (ECM) (e.g. qualitative and quantitative changes in the composition of tubular basement membranes (TBMs), interstitial matrix, tubular atrophy, and the accumulation of myofibroblasts. This fibrotic process leading to a decrease in the number of functioning nephrons is still not clear and constitutes the key of CKD progression.

More precisely, Kidney Disease Improving Global Outcomes (KDIGO) developed and published for the first time a system for the definition and classification of stages of CKD. Thus, CKD has been defined according to the criteria listed in according to the KDOQI CKD classification Table 11 (on the basis of reduction of glomerular filtration rate (GFR) in combination with signs of kidney damage) as reproduced in Table 1 below):

TABLE 1

Definition of Chronic Kidney Disease Criteria

1. Kidney damage for ≥3 months, as defined by structural or functional abnormalities of the kidney, with or without decreased GFR, manifest by either:
Pathological abnormalities; or
Markers of kidney damage, including abnormalities in the composition of the blood or urine, or abnormalities in imaging tests
2. GFR < 60 mL/min/1.73 $m^2$ for ≥3 months, with or without kidney damage Methods to estimate GFR are disuse in Guideline 4.
Markers of kidney damage are discussed in Guidelines 5-6.

A "subject" in the context of the present invention is a human (male or female). Typically said subject has been previously diagnosed with a disease leading to CKD.

In one embodiment, the patient in need thereof is suffering from a disease selected from the group consisting of nephropathy (e.g. membranous nephropathy (MN), diabetic nephropathy and hypertensive nephropathy), glomerulonephritis (e.g. membranous glomerulonephritis and membranoproliferative glomerulonephritis (MPGN) such as rapidly progressive glomerulonephritis (RPGN)), interstitial nephritis, lupus nephritis, idiopathic nephrotic syndrome (INS) (e.g. minimal change nephrotic syndrome (MCNS) and focal segmental glomerulosclerosis (FSGS)), obstructive uropathy, polycystic kidney disease (e.g. Autosomal Dominant Polycystic Kidney Disease (ADPKD) and Autosomal Recessive Polycystic Kidney Disease (ARPKD)), cardiovascular diseases, hypertension, diabetes, and kidney graft rejection (e.g. acute and chronic kidney rejection).

In one embodiment, the agent is an antibody or a portion thereof. In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of periostin. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the recombinant periostin may be provided by expression with recombinant cell lines. Recombinant form of periostin may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDRS). The CDRs, and in particular the CDRS regions, and more particularly the heavy chain CDRS, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., *I. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Mcdarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

Then, for this invention, once antibodies which bind to periostin have been obtained, neutralizing antibodies of periostin are selected. Accordingly, in a particular embodiment, the antibody which binds to periostin is a neutralizing anti-periostin antibody (i.e. an antibody which blocks the activity of periostin leading to the prevention of renal fibrosis and excessive accumulation of extracellular matrix (ECM) in the kidney.

An example of neutralizing antibody (MZ-1) has been described in Zhu et al., 20011 which is incorporated herein by reference.

Methods for obtaining neutralizing anti-periostin antibodies are well known from the skilled man in the art as those disclosed in the patent application EP1978034.

In another embodiment, the agent is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then, for this invention, neutralizing aptamers of periostin are selected.

In another embodiment, the agent is a polypeptide. In a particular embodiment the polypeptide is a functional equivalent of an extracellular matrix protein or an adhesion receptor which is capable of binding to periostin. As used herein, "an extracellular matrix protein" is a protein selected from the group consisting of fibronectin, tenascin-C, collagens (e.g. type I and V collagen). As used herein, "an adhesion receptor is a receptor selected from the group consisting of integrins (e.g. αvβ3, αvβ5 and α6β4).

As used herein, a "functional equivalent of an extracellular matrix protein or an adhesion receptor" is a compound which is capable of binding to periostin. The term "functional equivalent" includes fragments, mutants, and muteins of an extracellular matrix protein or an adhesion receptor. The term "functionally equivalent" thus includes any equivalent of an extracellular matrix protein or an adhesion receptor obtained by altering the amino acid sequence, for example by one or more amino acid deletions, substitutions or additions such that the protein analogue retains the ability to bind to periostin. Amino acid substitutions may be made, for example, by point mutation of the DNA encoding the amino acid sequence. Preferably, the functional equivalent is at least 80% homologous to the corresponding protein. In a preferred embodiment, the functional equivalent is at least 90% homologous as assessed by any conventional analysis algorithm such as for example, the Pileup sequence analysis software (Program Manual for the Wisconsin Package, 1996). It is envisaged that such molecules will be useful for the prevention or treatment of CKD since these molecules will bind specifically to periostin, and thus prevent renal fibrosis induced by periostin and finally prevent or treat CKD. As used herein, "binding specifically" means that the functionally equivalent analogue has high affinity for periostin but not for control proteins. Specific binding may be measured by a number of techniques such as ELISA, flow cytometry, western blotting, or immunoprecipitation. Preferably, the functionally equivalent analogue specifically binds to periostin at nanomolar or picomolar levels.

The polypeptides of the invention may be produced by any suitable means, as will be apparent to those of skill in the art. In order to produce sufficient amounts of an extracellular matrix protein, an adhesion receptor or functional equivalents thereof for use in accordance with the present invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known.

When expressed in recombinant form, the polypeptide is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E. coli*.

In specific embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and c-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

The present invention further relates to an agent which binds to periostin selected from the group consisting of antibodies, aptamers, small organic molecules and polypeptides for preventing or reducing renal fibrosis.

Another object of the present invention relates to an inhibitor of periostin gene expression for use in the prevention or the treatment of a CKD in a subject in need thereof.

An "inhibitor of expression" refers to a natural or synthetic compound that has a biological effect to inhibit the expression of a gene. Therefore, an "inhibitor of periostin gene expression" denotes a natural or synthetic compound that has a biological effect to inhibit the expression of periostin gene.

In a preferred embodiment of the invention, said inhibitor of periostin gene expression is a siRNA, an antisense oligonucleotide or a ribozyme.

Inhibitors of periostin gene expression for use in the present invention may be based on antisense oligonucleotide constructs. Anti-sense oligonucleotides, including anti-sense RNA molecules and anti-sense DNA molecules, would act to directly block the translation of periostin mRNA by binding thereto and thus preventing protein translation or increasing mRNA degradation, thus decreasing the level of periostin, and thus activity, in a cell. For example, antisense oligonucleotides of at least about 15 bases and complementary to unique regions of the mRNA transcript sequence encoding periostin can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

It should be further noted that antisense oligonucleotides may be modified with phosphorothioate to prevent their in vivo hydrolysis by nucleases. Such modifications arc' well known from the skilled man in the art.

In one embodiment, the sequence of the anti-sense oligonucleotide targeting periostin is represented by SEQ ID NO: 1.

In one embodiment, the sequence of the anti-sense oligonucleotide targeting periostin is represented by SEQ ID NO: 2.

Small inhibitory RNAs (siRNAs) can also function as inhibitors of periostin gene expression for use in the present invention. periostin gene expression can be reduced by contacting the tumor, subject or cell with a small double stranded RNA (dsRNA), or a vector or construct causing the production of a small double stranded RNA, such that periostin gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of periostin gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of periostin mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of periostin gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing periostin. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

The present invention further relates to an inhibitor of periostin gene expression for preventing or reducing renal fibrosis.

Another object of the invention relates to a method for the prevention or treatment of CKD comprising a step of administering a therapeutically effective amount of at least one agent which binds to periostin selected from the group consisting of antibodies, aptamers, small organic molecules and polypeptides or an inhibitor of periostin gene expression to a subject in need thereof.

Another object of the invention relates to a method for preventing or reducing renal fibrosis comprising a step of administering a therapeutically effective amount of at least one agent which binds to periostin selected from the group consisting of antibodies, aptamers, small organic molecules and polypeptides or an inhibitor of periostin gene expression to a subject in need thereof.

By a "therapeutically effective amount" of the agent or inhibitor of periostin gene expression as above described is meant a sufficient amount of the agent or inhibitor to prevent or treat CKD. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The agent which binds to periostin or inhibitor of the periostin gene expression of the invention may be combined with pharmaceutically acceptable excipients, and optionally sustained-release matrices, such as biodegradable polymers, to form therapeutic compositions.

Thus, the present invention relates to a pharmaceutical composition for use in the prevention or treatment of CKD comprising an agent or an inhibitor according to the invention and a pharmaceutically acceptable carrier.

The present invention also relates to a pharmaceutical composition for preventing or reducing renal fibrosis comprising an agent or an inhibitor according to the invention and a pharmaceutically acceptable carrier.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The agent which binds to periostin or inhibitor of the periostin gene expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The agent which binds to periostin or inhibitor of the periostin gene expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1: Periostin expression is highly induced in the renal cortex of mice after Unilateral Ureteral Obstruction (UUO). A. Periostin mRNA; B. Periostin protein.

Figure 2:
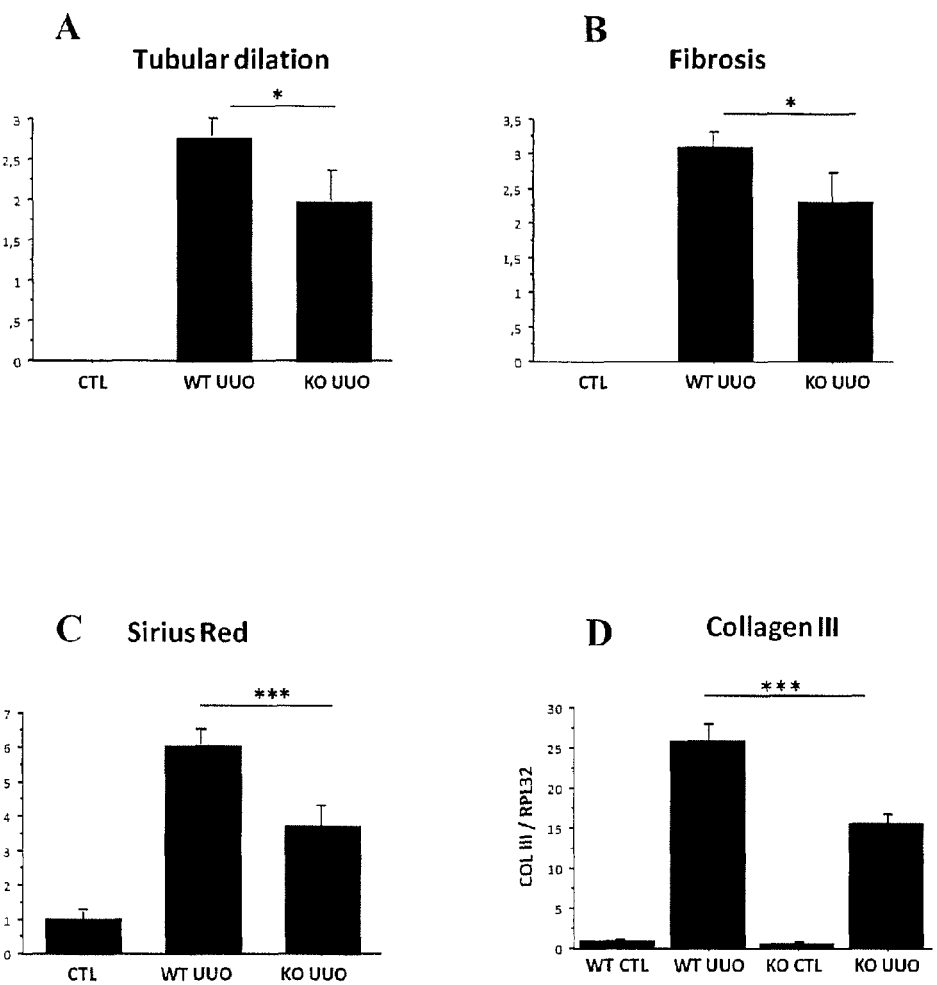

FIG. 2: Mice lacking periostin expression are protected against the typical structural alterations induced by UUO. A. Tubular dilation; B. Fibrosis; C. Fibrillar collagen accumulation (Sirius red-staining) and D. Collagen III mRNA expression.

Figure 3:
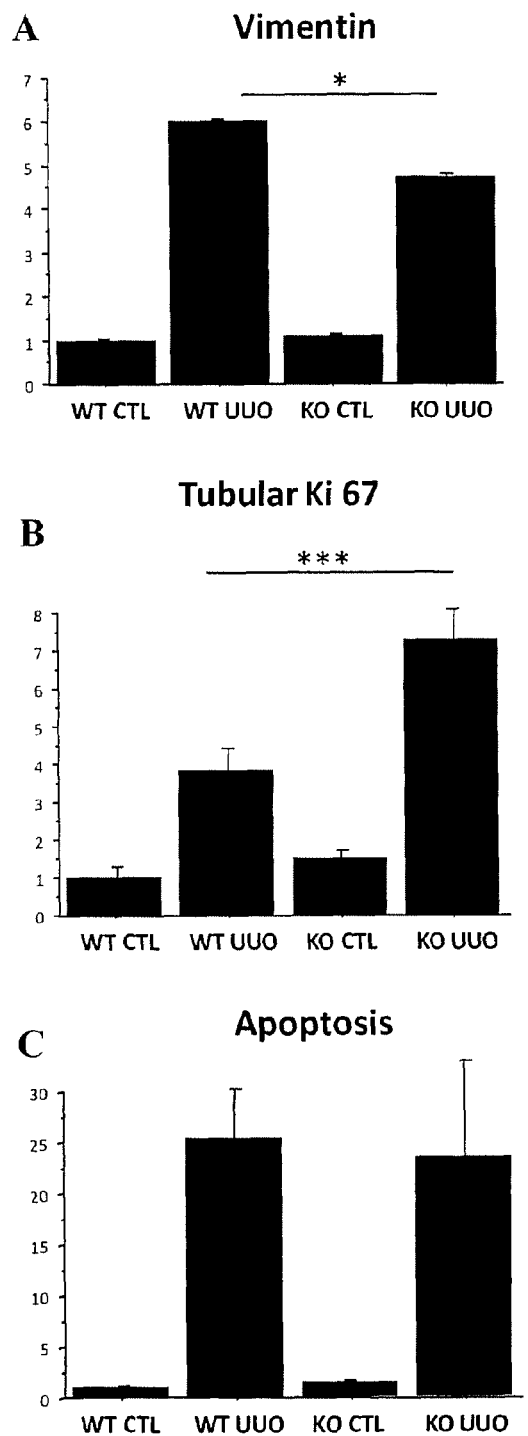
Figure 4:
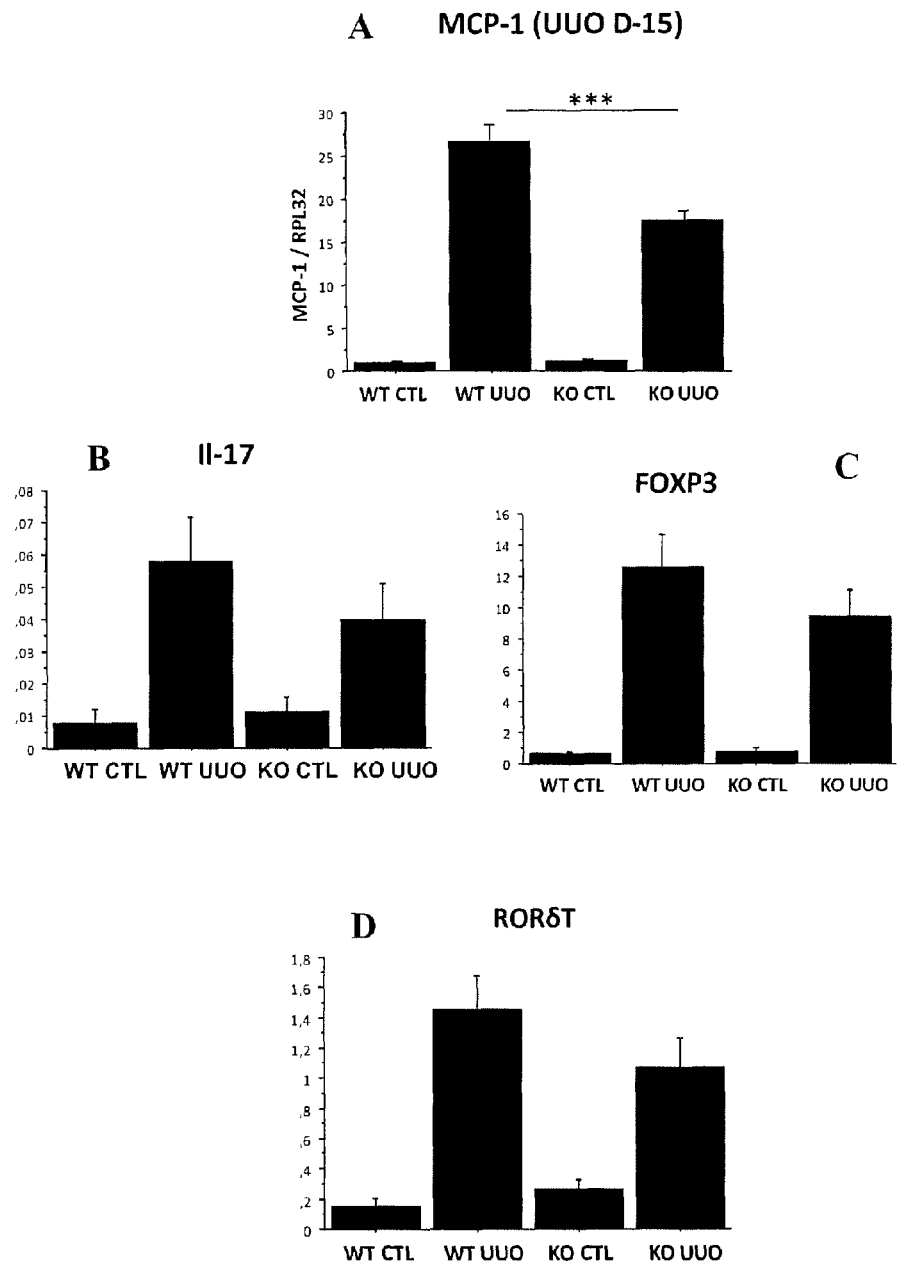

FIG. 3: Mice lacking periostin expression display a better degree of renal parenchyma preservation following UUO. A. Tubular preservation (Vimentin RNA expression); B. Cellular proliferation (Ki 67 immunostaining); C. Apoptosis FIG. 4: Mice lacking periostin expression have a blunted inflammatory response after UUO. A. MCP-1 RNA expression; B. IL-17 RNA expression; C. Foxp3 RNA expression; D. RORδT RNA expression.

Figure 5:
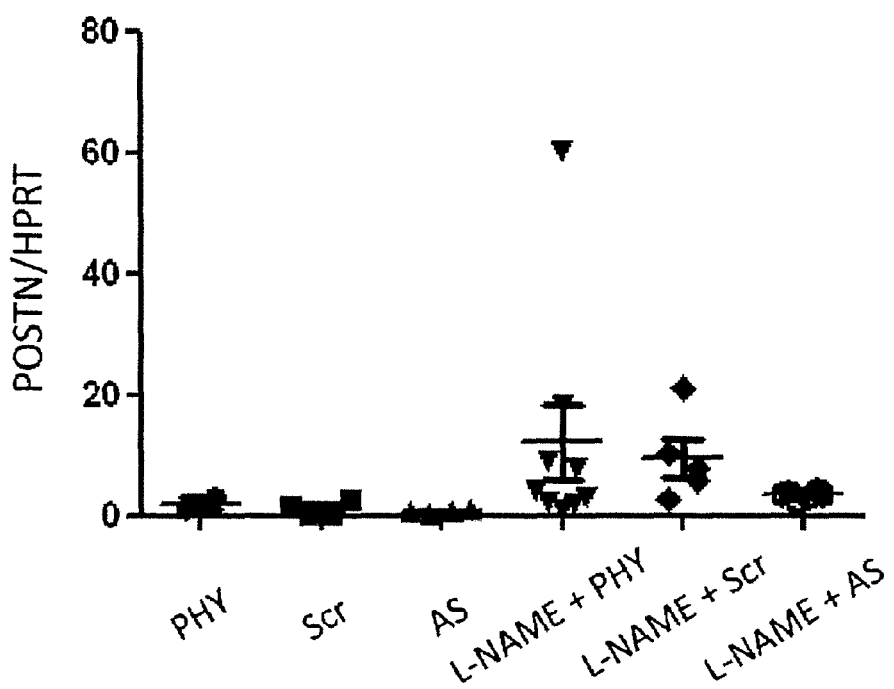

FIG. 5: In vivo specific ODN antisense delivery decreases periostin expression in the kidneys of hypertensive (L-NAME model) rats.

Figure 6:
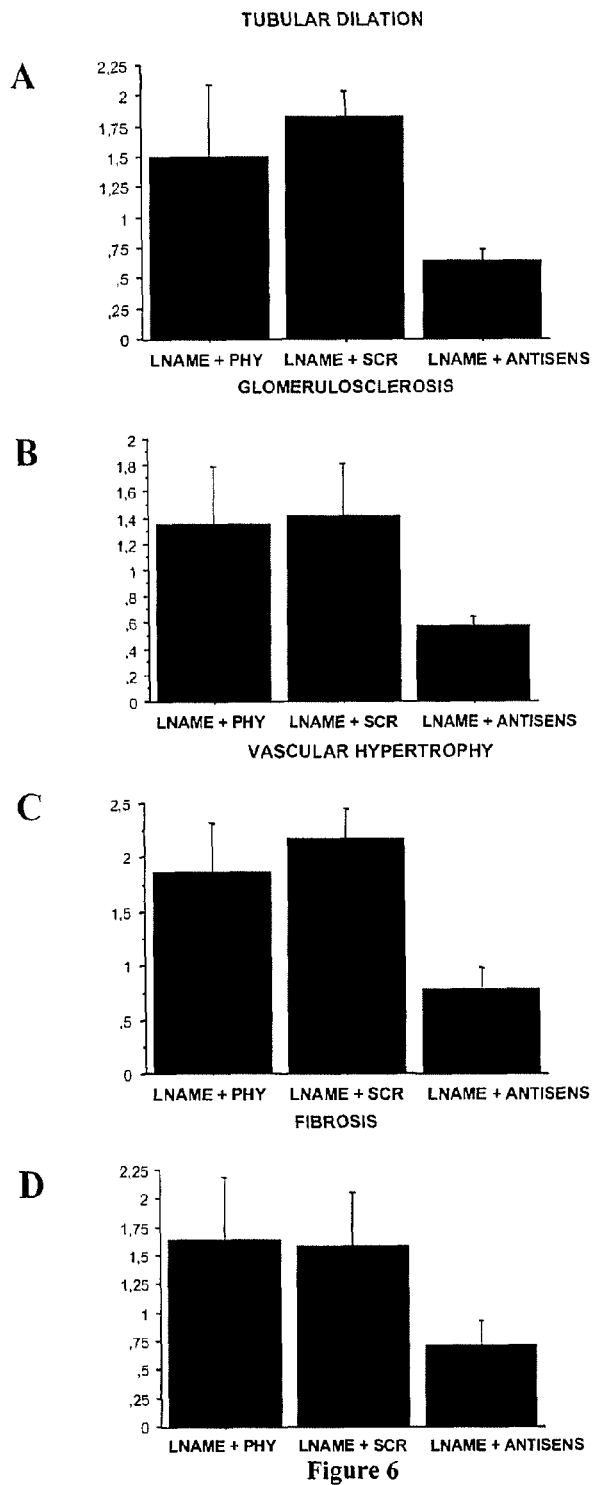

FIG. 6: In vivo administration of specific periostin antisense ODN blunted the typical structural alterations observed in hypertensive nephropathy in rats. A. Tubular dilation; B. Glomerulosclerosis; C. Vascular Hypertrophy; D. Fibrosis.

Figure 7:
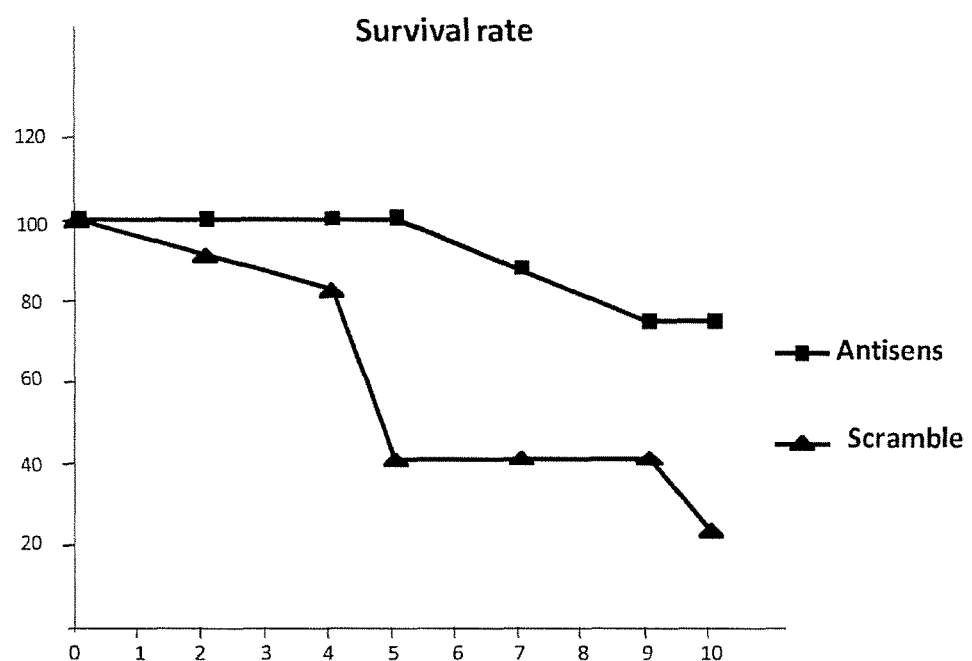

FIG. 7: Administration of specific periostin antisense ODN in hypertensive rats in which proteinuria exceeded 2 grams substantially decreased mortality rates.

EXAMPLES: PERIOSTIN, AN EXTRACELLULAR PROTEIN INVOLVED IN THE DEVELOPMENT OF CKD

Example 1: Periostin KO Mice are Protected Against the Development of CKD in an Experimental Tubulointerstitial Nephropathy (UUO Model)

Material & Methods

Animals:

Experiments were performed on wild type and periostin null mice (POSTN KO) donated kindly by S. J. Conway (Indianapolis, Ind.). These mice are characterized by the lack of the periostin gene and the replacement of the translation start site and the first exon by a lacZ reporter gene (ref). C57BL/6 WT and POSTN KO female mice aged 4 to 6 months were used (n=9). Tubulointerstitial nephropathy model was induced by the unilateral ureteral obstruction (UUO). After induction of general anesthesia (intraperitoneal injection of pentobarbital 50 mg/kg), POSTN KO mice and WT counterparts were subjected to a left flank incision. UUO was performed by complete ligation of the left ureter at the ureteropelvic junction, using double silk sutures. Controlateral kidneys were used as controls. Mice were sacrificed at day 15.

Animals were maintained with free access to standard chow and tap water during the protocols. They were sacrificed under general anesthesia (pentobarbital 150 mg/kg). Kidneys were removed and divided in four equal parts (for RNA, protein, cryosections and paraffin sections). All procedures were in accordance with European Union Guidelines for the Care and the use of laboratory animals and were approved the local ethic committee.

Renal Histology:

Kidneys were immersed 24 h in alcohol-formalin-acetic acid (AFA) and then embedded in paraffin wax prior to sectioning. The tissues were cut into 4-μm sections and stained with Masson's trichrome. The slides were independently examined on a blinded basis for the level of tubular dilation, perivascular fibrosis (for mice and rats), glomerulosclerosis and vascular hypertrophy (for rats), using a 0 to 4 injury scale as described previously. The mean value was used to compare the animals' groups.

Sirius Red:

Interstitial fibrosis was assessed on 4 μm-thick Sirius red-stained paraffin sections at 40× magnification, under polarized light. Five cortical fields excluding interlobular arteries were selected randomly from each kidney and the red-stained area per total area, reflecting interstitial fibrosis, was quantified using computer-based morphometric analysis software (Axionplan, Axiophot2, Zeiss, Germany). Scoring was performed in a blinded manner on coded slides. Data are expressed as the mean value of the percentage of positive area examined.

IHC:

Staining for periostin was performed on 5 μm frozen sections. Sections were incubated with monoclonal rat anti-mouse periostin antibody (R&D Systems, 1/1000), for one hour at 37° C. To stain proliferation, T lymphocytes and macrophages, 5 μm sections of paraffin-embedded kidneys were dewaxed, heated in citric acid solution (pH6) at 98° C. for 30 min, and respectively incubated with: Ki 67 (polyclonal rabbit, Abcam, 1/1000), CD3 (mouse anti-human, Dako 1/200), F4/80 (monoclonal rat anti-mouse, AbD Serotec, 1/200).

Secondary antibodies are from N-Histofine kit (Nichirei Biochemicals, Japan). They were incubated for 30 min at room temperature. Staining was revealed by applying AEC (Dako), counterstained with hematoxylin QS (Vector, Burlingame, Calif.), and finalized with Permanent Aqueous Mounting Media (Innovex).

β-Gal Staining:

B-gal staining was described by J S. Duffield et al. Tissues were fixed with 4% PFA at 4° C. for one hour, transferred to PBS containing 18% sucrose overnight (4° C.), and then stored at −80° C. 5 μm sections were cut, washed in PBS for 10 minutes, incubated in blocking buffer (1 mM MgCl2, 0.01% Na-deoxycholate, 0.02% IGEPAL-CA630, and 5 mMEGTA in PBS) for 20 minutes at room temperature, and incubated in the X-gal mixture [1 mM MgCl2, 0.01% Na-deoxycholate, 0.02% 1GEPAL-CA630, 5 mM EGTA, 5 mM K3Fe(CN)6, 5 mM K4Fe(CN)6.3H2O, and 1 μg X-gal; all from invivogen)]; Care was taken to perform X-gal staining at neutral pH and the incubation was carried out for 16 hours at 37° C. After 5 min PBS wash, the sections were counterstained with eosin (Sigma-Aldrich, St. Louis, Mo.) and mounted.

In Situ End-Labeling for the Detection of Apoptotic Cells:

To detect apoptotic cells, 5 μm tissue sections fixed in AFA and embedded in paraffin were stained by the TUNEL assay, using ApopTag Plus, peroxidase Kit (Qbiogen, France S7101-KIT) according to the manufacturer's instructions. For each kidney section, the whole cortical area was analyzed at 40× magnification. The number of stained apoptotic cells by power field was counted manually and the mean value was used to compare the animals.

PCR:

The inventors extracted RNA from the renal cortex using TRIzol solution (Life Technologies BRL, Gaithersburg, Md.). RNA quality was checked by measuring the ratio of optical densities at 260 and 280 nm and residual genomic DNA was removed by DNase I treatment for 30 min at 37° C. (Fermentas). The inventors used reverse transcription with Revert Aid H minus First Strand DNA Synthesis kit (Fermentas) to convert 1 μg RNA into cDNA. Transcriptomic analyses were performed with RT$^2$Profiler PCR Array (Superarray, Bioscience Corp, Tebu Bio, Le Perray en Yvelines, France). cDNA was amplified by PCR using a LightCycler 480 (Roche Diagnostic) using SYBR Green (Fast Start DNA Master SYBRGreen I; Roche Applied Science, Roche Diagnostic), specific primers for selected mRNA and 60S ribosomal protein L32 (RPL32) housekeeping gene under the following conditions: 95° C. for 5 min, and 45 cycles at 95° C. for 15 s and 60° C. for 15 s, then 72° C. for 15 s. Specific primers were designed by Universal Probe Library system (UPL, Roche Applied Science). To normalize the qRT-PCR results the inventors used Roche LightCycler 2.0 software (Roche Diagnostics). The inventors expressed results as 2-ΔCp, where Cp is the cycle threshold number. They analyzed dissociation curves after each run for every amplicon to assess the specificity of quantification when using SYBR Green.

Western Blot Analysis:

Proteins were extracted from renal cortex using RIPA buffer supplemented with protease inhibitor cocktail (Sigma-Aldrich). 20 μg of proteins diluted in SDS sample buffer were heated at 70° C. for 10 min, separated on a 4-15% tris-HCL gel and then transferred to a PVDF membrane (Thermo Scientific). After blocking in PBS 1×, 5% milk (thermoscientific) for 2 hours at room temperature, the membrane was incubated with the primary antibodies (Periostin, E-cadherin) overnight at 4° C., washed and incubated with secondary antibodies conjugated to horseradish peroxidase (SouthernBiotech or Vector) for 2 hours at room temperature. Protein bands were visualized using enhanced Supersignal® west picochemiluminescent reagents according to the manufacturer's instructions (Thermoscientific) and quantified using densitometry (Chemicapt, Fisher Bioblock scientific).

Statistics:

Statistical analyses were performed using ANOVA followed by Protected Least Significance. Difference Fisher test (Statview software). Results with $p<0.05$ were considered statistically significant. All values are means±SEM.

Results

Periostin Expression is Induced after UUO:

Periostin messenger RNA (mRNA) examined by RT-qPCR, shows a very low baseline expression of periostin in the control kidneys. This expression is 50-fold upregulated at day 15 after obstruction (FIG. 1A). This finding is confirmed by immunoblotting that shows no periostin in control kidneys and a significant induction of renal periostin at day 5 and day 15 after UUO (FIG. 1B). In order to follow the emergence and the localization of periostin, the inventors performed a β-galatosidase staining in KO mice and an immunostaining for the corresponding WT at day 2, day 5 and day 15 after UUO. The β-galatosidase and periostin staining was not detected in all control kidneys. After UUO, β-galatosidase shows that periostin expression starts in collecting duct epithelial cells (day 2), then in tubular epithelial cells (day 5, day 15) and in interstitial cells (day 15). The immuno-histochemistry shows an interstitial staining for periostin that starts in the medulla (day 2) and expand to cortex (day 5, day 15). Taken together, this data demonstrate that periostin expression is induced by UUO and correlates with the progression of the injury.

Periostin Null Mice are Protected Against Tubular Dilation and Fibrosis Induced by UUO:

Evaluation of renal histology was assessed by Masson's trichrom staining on normal and obstructed kidneys. 15 days after UUO, KO mice show less tubular dilation (FIG. 2A) and less fibrosis (FIG. 2B). To underscore fibrillar collagen accumulation, renal sections were Sirius red-stained and the morphometric analysis proved that KO mice had less fibrillar collagen comparing to WT (FIG. 2C). This data was confirmed by collagen III mRNA expression assessed by RT-qPCR (FIG. 2D).

Periostin Null Mice Present a Better Preservation of Epithelial Tubular Cells:

To elucidate the difference observed between WT and KO mice in terms of tubular dilation, the inventors examined cellular proliferation (FIG. 3B), tubular preservation (FIG. 3A) and apoptosis (FIG. 3C). Proliferation was assessed by Ki 67 immunostaining (proliferative cell marker); tubular preservation was demonstrated by vimentin RNA expression (mensenchymal cell marker) and E-cadherin protein level (epithelial cell adhesion molecule). Apoptosis was evaluated by TUNNEL. At Day 15, epithelial tubular cells proliferate more in the obstructed kidney of KO mice comparing to the WT. The increase of vimentin RNA level was concomitant with the loss of E-cadherin for WT mice, whereas KO mice showed less increase of vimentin and maintenance of E-cadherin. On the contrary, apoptotic cells were similarly increased in WT and KO mice after UUO.

Periostin and Inflammation:

Obstructive nephropathy is characterized by an inflammatory response in the kidney that contributes to tubular atrophy and interstitial fibrosis. Since the POSTN KO mice were protected in terms of fibrosis and tubular damage, the inventors investigated inflammation. Interestingly, after UUO, RT-qPCR showed that monocyte chemoattractant protein-1 (MCP-1) upregulation was significantly blunted in POSTN KO mice (FIG. 4A). However, there was no significant difference between POSTN KO and WT mice for IL-17 (FIG. 4B) or RORδT/Foxp3 expression (FIGS. 4C and 4D). Macrophages infiltration was evaluated by IHC, no difference in F4/80+ cells was observed 15 days after UUO.

Example 2: Periostin Antisense Oligonucleotide Periostin Protect Against the Development of in a Hypertensive Nephropathy Rat Model (L-NAME Treated Rats)

Material & Methods

Animals:

Male Sprague-Dawley rats, weighing 250 g, were maintained on a normal-salt diet and had free access to chow and water. To induce a hypertensive nephropathy model, LNAME, an inhibitor of NO synthesis, was given via drinking water at the dose of 30 mg/kg/day. In order to investigate the role of periostin, the inventors used an antisense approach to down regulate its expression.

Administration of Antisense (AS) Against Periostin:

To block periostin expression, the inventors used a specific AS oligodeoxynucleotides (ODN) modified with phosphorothioate to prevent their in vivo hydrolysis by nucleases. The AS or scrambled control ODNs were administered by intraperitoneal (IP, 1 μM) either in a preventive or curative way. In the preventive protocol, antisense injection started with LNAME administration and rats were sacrificed at day 19. However, in the curative protocol, antisense injection started after LNAME administration, when rats reached a proteinuria of 1 g/mmol. LNAME was maintained but the dose was decreased to 15 mg/kg/day and rats were sacrificed one week after antisense treatment.

Results

As shown in FIG. 5, in vivo specific ODN antisense delivery decreases periostin expression in the kidneys of hypertensive (L-NAME model) rats. As shown in FIG. 6, in vivo administration of specific periostin antisense ODN blunted the typical structural alterations observed in hypertensive nephropathy in rats (i.e. tubular dilation, glomerulosclerosis, vascular hypertrophy and fibrosis). Moreover, as shown in FIG. 7, administration of specific periostin antisense ODN in hypertensive rats in which proteinuria exceeded 2 grams substantially decreased mortality rates demonstrating the interest of targeting periostin (e.g. by inhibitor of periostin gene expression or by an anti-periostin neutralizing antibody or aptamer) for preventing and also for treating CKD.

CONCLUSION

The inventors have shown that periostin is involved in the development of CKD by promoting renal fibrosis and excessive accumulation of ECM in the kidney by using two distinct models as previously described. It results that agents which binds periostin (e.g. anti-periostin neutralizing antibody or aptamer) and inhibitors of periostin gene expression) are useful for preventing renal fibrosis and excessive accumulation of ECM in the kidney and are therefore useful in the prevention or the treatment of CKD in a subject in need thereof.

REFERENCES

Throughout this application, various references describe the state of the art to which this invention pertains. The disclosures of these references are hereby incorporated by reference into the present disclosure.

Guerrot D, Dussaule J C, Mael-Ainin M, Xu-Dubois Y C, Rondcau E, Chatziantoniou C, Placier S. Identification of periostin as a critical marker of progression/reversal of hypertensive nephropathy. PLoS One. 2012; 7(3):e31974.

Wallace D P, Quante M T, Reif G A, Nivens E, Ahmed F, Hempson S J, Blanco G, Yamaguchi T. Periostin induces proliferation of human autosomal dominant polycystic kidney cells through alphaV-integrin receptor. Am J Physiol Renal Physiol. 2008 November; 295(5):F1463-71

Zhu M, Saxton R E, Ramos L, Chang D D, Karlan B Y, Gasson J C, Slamon D J. Neutralizing monoclonal antibody to periostin inhibits ovarian tumor growth and metastasis. Mol Cancer Ther. 2011 August; 10(8):1500-8.

The invention claimed is:

1. A method of reducing renal fibrosis in a subject in need thereof, comprising
administering to the subject a therapeutically effective amount of an inhibitor of periostin gene expression, wherein said inhibitor is an antisense oligonucleotide that is complementary to at least 15 bases of a gene encoding periostin.

2. The method according to claim 1, wherein the subject in need thereof is suffering from a disease selected from the group consisting of nephropathy, glomerulonephritis, interstitial nephritis, lupus nephritis, idiopathic nephrotic syndrome (INS), obstructive uropathy, polycystic kidney disease, cardiovascular disease, hypertension, diabetes, and kidney graft rejection.

3. A pharmaceutical composition for use in reducing renal fibrosis or reducing accumulation of extracellular matrix (ECM) in a kidney consisting of an inhibitor of periostin gene expression, wherein said inhibitor is an antisense oligonucleotide having the sequence of SEQ ID NO: 2; and a pharmaceutically acceptable carrier.

4. The method of claim 2, wherein said nephropathy is selected from the group consisting of membranous nephropathy (MN), diabetic nephropathy and hypertensive nephropathy.

5. The method of claim 2, wherein said glomerulonephritis is selected from the group consisting of membranous glomerulonephritis, membranoproliferative glomerulonephritis (MPGN) and rapidly progressive glomerulonephritis (RPGN).

6. The method of claim 2, wherein said INS is selected from the group consisting of minimal change nephrotic syndrome (MCNS) and focal segmental glomerulosclerosis (FSGS).

7. The method of claim 2, wherein said polycystic kidney disease is selected from the group consisting of Autosomal Dominant Polycystic Kidney Disease (ADPKD) and Autosomal Recessive Polycystic Kidney Disease (ARPKD).

8. The method of claim 2, wherein said kidney graft rejection disease is selected from the group consisting of acute kidney rejection and chronic kidney rejection.

9. A method of reducing accumulation of extracellular matrix (ECM) in a kidney of a subject in need thereof, comprising
administering to the subject a therapeutically effective amount of an inhibitor of periostin gene expression, wherein said inhibitor is an antisense oligonucleotide that is complementary to at least 15 bases of a gene encoding periostin.

10. The method according to claim 9, wherein the subject in need thereof is suffering from a disease selected from the group consisting of nephropathy, glomerulonephritis, interstitial nephritis, lupus nephritis, idiopathic nephrotic syndrome (INS), obstructive uropathy, polycystic kidney disease, cardiovascular disease, hypertension, diabetes, and kidney graft rejection.

11. The method of claim 10, wherein said nephropathy is selected from the group consisting of membranous nephropathy (MN), diabetic nephropathy and hypertensive nephropathy.

12. The method of claim 10, wherein said glomerulonephritis is selected from the group consisting of membranous glomerulonephritis, membranoproliferative glomerulonephritis (MPGN) and rapidly progressive glomerulonephritis (RPGN).

13. The method of claim 10, wherein said INS is selected from the group consisting of minimal change nephrotic syndrome (MCNS) and focal segmental glomerulosclerosis (FSGS).

14. The method of claim 10, wherein said polycystic kidney disease is selected from the group consisting of Autosomal Dominant Polycystic Kidney Disease (ADPKD) and Autosomal Recessive Polycystic Kidney Disease (ARPKD).

15. The method of claim 10, wherein said kidney graft rejection disease is selected from the group consisting of acute kidney rejection and chronic kidney rejection.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial
<220> FEATURE:
<223> OTHER INFORMATION: Synthetic antisense (AS) oligodeoxynucleotides
      (ODN) against periostin

<400> SEQUENCE: 1
gagaggaacc atcttcagcc ctgagctccg                                    30

<210> SEQ ID NO 2
<211> LENGTH: 21
<212> TYPE: DNA
```

```
<213> ORGANISM: Artificial
<220> FEATURE:
<223> OTHER INFORMATION: Synthetic antisense (AS) oligodeoxynucleotide
      (ODN) against periostin

<400> SEQUENCE: 2
tctccctcac accctatttc a                                              21
```